(12) United States Patent
Ecke et al.

(10) Patent No.: US 12,114,944 B2
(45) Date of Patent: *Oct. 15, 2024

(54) EFFICIENT POSITIONING OF A MECHATRONIC ARM

(71) Applicant: Brainlab AG, Munich (DE)

(72) Inventors: Karolin Ecke, Munich (DE); Nils Frielinghaus, Heimstetten (DE)

(73) Assignee: Brainlab AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/126,769

(22) Filed: Mar. 27, 2023

(65) Prior Publication Data

US 2023/0293248 A1   Sep. 21, 2023

Related U.S. Application Data

(63) Continuation of application No. 15/770,684, filed as application No. PCT/EP2017/071285 on Aug. 24, 2017, now Pat. No. 11,642,182.

(51) Int. Cl.
  *A61B 34/30* (2016.01)
  *A61B 34/20* (2016.01)
  (Continued)

(52) U.S. Cl.
  CPC ............ *A61B 34/30* (2016.02); *A61B 34/20* (2016.02); *A61B 90/50* (2016.02); *G16H 40/63* (2018.01);
  (Continued)

(58) Field of Classification Search
  CPC ......... A61B 34/30; A61B 34/20; A61B 90/50; A61B 2034/2055; A61B 2034/2057;
  (Continued)

(56) References Cited

U.S. PATENT DOCUMENTS

| 4,143,652 A | * | 3/1979 | Meier | A61B 90/50 600/230 |
| 5,389,101 A | * | 2/1995 | Heilbrun | A61B 34/20 348/E13.016 |

(Continued)

FOREIGN PATENT DOCUMENTS

| CN | 105327438 | 2/2016 |
| CN | 109589145 | 4/2019 |

(Continued)

OTHER PUBLICATIONS

"Computer-Assisted Orthopedic Surgery: Current State and Future Perspective;" Zheng et al. ; Frontiers in Surgery, 2, 66; Dec. 23, 2015. (Year: 2015).*

(Continued)

*Primary Examiner* — Khoi H Tran
*Assistant Examiner* — Jorge O Peche
(74) *Attorney, Agent, or Firm* — Tucker Ellis LLP

(57) ABSTRACT

A computer-implemented medical data processing method for controlling a geometric status of a mechatronic articulable arm. Current geometric status data is acquired describing a current geometric status of the mechatronic articulable arm defined by a set of current spatial relationship between connected elements of the mechatronic articulable arm. Changed geometric status data describing a changed geometric status of the mechatronic articulable arm defined by a set of changed spatial relationship between the connected elements is determined based on current device position data, the current geometric status data, changed device position data, and device definition data. Instruction data describing an instruction for changing the geometric status of the mechatronic articulable arm from the current geometric status to the changed geometric status is determined. The (Continued)

instruction describes changes from the current spatial relationship to the changed spatial relationship.

20 Claims, 5 Drawing Sheets

(51) Int. Cl.
    *A61B 90/50*         (2016.01)
    *G16H 40/63*       (2018.01)

(52) U.S. Cl.
    CPC ............ *A61B 2034/2055* (2016.02); *A61B 2034/2057* (2016.02); *A61B 2034/2072* (2016.02); *A61B 2034/301* (2016.02); *A61B 2090/508* (2016.02)

(58) Field of Classification Search
    CPC ...... A61B 2034/2072; A61B 2034/301; A61B 2090/508; G16H 40/63
    See application file for complete search history.

(56) References Cited

U.S. PATENT DOCUMENTS

| | | | | |
|---|---|---|---|---|
| 5,603,318 | A * | 2/1997 | Heilbrun | H04N 13/239 348/E13.016 |
| 5,971,976 | A * | 10/1999 | Wang | A61B 34/77 600/595 |
| 6,231,565 | B1 * | 5/2001 | Tovey | A61B 34/30 606/1 |
| 6,484,049 | B1 * | 11/2002 | Seeley | A61B 90/36 600/431 |
| 6,546,279 | B1 * | 4/2003 | Bova | A61B 90/17 600/439 |
| 6,642,686 | B1 * | 11/2003 | Ruch | A61B 34/70 318/568.14 |
| 6,846,282 | B1 * | 1/2005 | Ford | A61N 5/1007 600/1 |
| 6,885,886 | B2 * | 4/2005 | Bauch | G06T 19/00 600/416 |
| 7,203,277 | B2 * | 4/2007 | Birkenbach | A61B 6/032 378/205 |
| 7,302,288 | B1 * | 11/2007 | Schellenberg | A61B 34/20 606/130 |
| 8,306,656 | B1 * | 11/2012 | Schaible | A61B 34/71 700/245 |
| 8,444,631 | B2 * | 5/2013 | Yeung | A61B 34/30 606/1 |
| 8,750,965 | B2 * | 6/2014 | Woerlein | A61B 90/02 600/424 |
| 9,033,998 | B1 * | 5/2015 | Schaible | A61B 34/30 606/130 |
| 9,387,048 | B2 * | 7/2016 | Donhowe | A61M 25/0127 |
| 9,427,872 | B1 * | 8/2016 | Bingham | G01D 5/2448 |
| 10,016,900 | B1 * | 7/2018 | Meyer | A61B 34/30 |
| 10,238,837 | B2 * | 3/2019 | Duindam | A61B 34/30 |
| 10,603,120 | B2 * | 3/2020 | Steinle | A61B 34/20 |
| 10,772,577 | B2 * | 9/2020 | Fortuna | A61B 34/30 |
| 10,898,286 | B2 * | 1/2021 | Srinivasan | A61B 34/20 |
| 11,096,709 | B1 * | 8/2021 | Chin | A61B 34/30 |
| 11,207,137 | B2 * | 12/2021 | Veigel | A61N 5/1049 |
| 11,246,665 | B2 * | 2/2022 | Varkuti | A61B 34/20 |
| 11,464,590 | B1 * | 10/2022 | Roh | G16H 40/63 |
| 11,510,635 | B2 * | 11/2022 | Fortuna | A61B 6/4405 |
| 11,628,012 | B2 * | 4/2023 | Veigel | A61N 5/1048 600/595 |
| 11,642,182 | B2 * | 5/2023 | Ecke | G16H 40/63 600/476 |
| 11,786,319 | B2 * | 10/2023 | Johnson | A61B 34/30 715/761 |
| 11,813,033 | B2 * | 11/2023 | Campagna | B25J 9/101 |
| 2002/0032375 | A1 * | 3/2002 | Bauch | A61B 6/5247 600/407 |
| 2003/0088179 | A1 * | 5/2003 | Seeley | A61B 6/487 600/424 |
| 2003/0130576 | A1 * | 7/2003 | Seeley | A61B 90/36 600/426 |
| 2004/0049121 | A1 * | 3/2004 | Yaron | A61B 5/24 600/544 |
| 2004/0172044 | A1 * | 9/2004 | Grimm | A61B 90/10 606/130 |
| 2006/0178556 | A1 * | 8/2006 | Hasser | A61B 1/0055 600/102 |
| 2006/0258938 | A1 * | 11/2006 | Hoffman | A61B 5/06 600/424 |
| 2007/0055144 | A1 * | 3/2007 | Neustadter | A61N 5/1049 600/425 |
| 2007/0083098 | A1 * | 4/2007 | Stern | A61B 34/35 600/407 |
| 2008/0183068 | A1 * | 7/2008 | Carls | A61B 5/4041 600/411 |
| 2008/0183074 | A1 * | 7/2008 | Carls | A61B 6/506 600/429 |
| 2008/0183188 | A1 * | 7/2008 | Carls | A61B 6/506 606/130 |
| 2008/0183189 | A1 * | 7/2008 | Teichman | A61B 6/506 606/130 |
| 2008/0183190 | A1 * | 7/2008 | Adcox | G16H 30/40 606/130 |
| 2010/0217117 | A1 * | 8/2010 | Glossop | A61B 34/20 600/424 |
| 2010/0249800 | A1 * | 9/2010 | Kim | A61B 6/4441 606/130 |
| 2011/0081063 | A1 * | 4/2011 | Leroy | A61B 8/0841 382/131 |
| 2011/0190790 | A1 * | 8/2011 | Summerer | A61B 34/76 606/130 |
| 2012/0136372 | A1 * | 5/2012 | Amat Girbau | A61B 34/30 606/130 |
| 2013/0172903 | A1 * | 7/2013 | Suarez | A61B 34/30 606/1 |
| 2013/0205558 | A1 * | 8/2013 | Sporer | F16M 11/10 29/407.01 |
| 2013/0267838 | A1 * | 10/2013 | Fronk | A61B 5/064 600/424 |
| 2013/0325029 | A1 * | 12/2013 | Hourtash | B25J 9/1607 606/130 |
| 2014/0073910 | A1 * | 3/2014 | Munrow | A61B 34/25 600/424 |
| 2014/0316431 | A1 * | 10/2014 | Hourtash | A61B 34/37 606/130 |
| 2014/0330432 | A1 * | 11/2014 | Simaan | B25J 9/1625 700/250 |
| 2016/0157942 | A1 * | 6/2016 | Gombert | A61B 34/30 606/130 |
| 2016/0184038 | A1 * | 6/2016 | Denissen | B25J 9/1633 901/9 |
| 2016/0310221 | A1 * | 10/2016 | Bar | A61B 90/06 |
| 2016/0361087 | A1 * | 12/2016 | Hamamoto | A61B 1/00147 |
| 2017/0066131 | A1 * | 3/2017 | Kamikawa | B25J 9/1697 |
| 2017/0079728 | A1 * | 3/2017 | Nawrat | A61B 34/30 |
| 2017/0143303 | A1 * | 5/2017 | Chen | A61B 8/488 |
| 2018/0028387 | A1 * | 2/2018 | Yellin | A61B 34/70 |
| 2018/0049829 | A1 * | 2/2018 | Yates | A61B 34/30 |
| 2018/0049830 | A1 * | 2/2018 | Yates | A61B 34/35 |
| 2018/0055591 | A1 * | 3/2018 | Bonny | A61B 90/57 |
| 2018/0132927 | A1 * | 5/2018 | Chen | A61B 18/18 |
| 2018/0207794 | A1 * | 7/2018 | Sebring | B25J 5/007 |
| 2018/0263714 | A1 * | 9/2018 | Kostrzewski | A61B 17/1703 |
| 2019/0000567 | A1 * | 1/2019 | Allen | A61B 34/30 |
| 2019/0005661 | A1 * | 1/2019 | Steinle | G06T 7/33 |
| 2019/0021800 | A1 * | 1/2019 | Crawford | G16H 40/63 |
| 2019/0038240 | A1 * | 2/2019 | Fortuna | A61B 34/30 |
| 2019/0046278 | A1 * | 2/2019 | Steinle | A61B 34/30 |
| 2019/0053862 | A1 | 2/2019 | Ecke et al. | |
| 2019/0125470 | A1 * | 5/2019 | Moskowitz | A61B 17/3403 |
| 2019/0175287 | A1 * | 6/2019 | Hill | A61B 34/30 |
| 2019/0192238 | A1 * | 6/2019 | Tsuboi | B25J 13/085 |
| 2019/0216560 | A1 * | 7/2019 | Bono | A61B 90/39 |
| 2019/0291277 | A1 * | 9/2019 | Oleynik | B25J 9/1669 |

(56) References Cited

U.S. PATENT DOCUMENTS

| | | | |
|---|---|---|---|
| 2019/0378276 A1* | 12/2019 | Flossmann | G06T 7/60 |
| 2020/0022763 A1* | 1/2020 | Hares | A61B 1/00128 |
| 2020/0069373 A1* | 3/2020 | Yu | A61B 34/74 |
| 2020/0110936 A1* | 4/2020 | Hares | G06V 20/41 |
| 2020/0146758 A1* | 5/2020 | Millahn | A61B 34/20 |
| 2020/0219254 A1* | 7/2020 | Regensburger | A61B 6/5264 |
| 2020/0229879 A1* | 7/2020 | Magaraggia | A61B 34/30 |
| 2020/0261161 A1* | 8/2020 | Frielinghaus | A61B 34/20 |
| 2020/0278080 A1* | 9/2020 | Erens | A61B 90/37 |
| 2020/0297434 A1* | 9/2020 | Bencteux | G21F 3/00 |
| 2020/0320714 A1* | 10/2020 | Sartor | G06T 7/13 |
| 2020/0337536 A1* | 10/2020 | Salcudean | A61B 34/37 |
| 2020/0405561 A1* | 12/2020 | Campagna | A61G 13/1265 |
| 2021/0000432 A1* | 1/2021 | Fortuna | A61B 6/4405 |
| 2021/0030501 A1* | 2/2021 | Eyre | A61B 34/37 |
| 2021/0100627 A1* | 4/2021 | Soper | G06T 7/74 |
| 2021/0121253 A1* | 4/2021 | Leibrandt | A61B 34/76 |
| 2021/0177526 A1* | 6/2021 | Goyette | A61B 34/20 |
| 2021/0178002 A1* | 6/2021 | Steinle | A61B 34/25 |
| 2021/0196397 A1* | 7/2021 | Peng | A61B 34/20 |
| 2021/0196399 A1* | 7/2021 | Ayvali | A61B 34/30 |
| 2021/0236207 A1* | 8/2021 | Stanton | A61B 34/74 |
| 2021/0244485 A1* | 8/2021 | Coiseur | A61B 90/361 |
| 2021/0315637 A1* | 10/2021 | Ida | A61B 34/30 |
| 2021/0322115 A1* | 10/2021 | DiMaio | A61B 46/10 |
| 2021/0361357 A1* | 11/2021 | Crawford | A61B 34/20 |
| 2021/0369359 A1* | 12/2021 | Blanckaert | B25J 9/1664 |
| 2021/0386606 A1* | 12/2021 | Campagna | A61G 13/06 |
| 2021/0393353 A1* | 12/2021 | Campagna | B25J 9/101 |
| 2022/0022980 A1* | 1/2022 | DiMaio | A61B 50/13 |
| 2022/0047259 A1* | 2/2022 | Prior | A61B 34/30 |
| 2022/0047337 A1* | 2/2022 | Kostrzewski | A61B 90/06 |
| 2022/0047339 A1* | 2/2022 | Prior | A61B 34/20 |
| 2022/0071708 A1* | 3/2022 | Veigel | G09B 19/003 |
| 2022/0151607 A1* | 5/2022 | Bowers | A61B 34/30 |
| 2022/0183778 A1* | 6/2022 | Stopp | A61B 34/25 |
| 2023/0068780 A1* | 3/2023 | Ichii | A61B 34/74 |
| 2023/0142404 A1* | 5/2023 | Ariki | B25J 9/163 600/102 |
| 2023/0181269 A1* | 6/2023 | Kreciglowa | A61B 34/74 606/1 |
| 2023/0190391 A1* | 6/2023 | Lavallée | A61B 34/30 606/1 |
| 2023/0190394 A1* | 6/2023 | Tam | A61B 34/37 606/1 |
| 2023/0202040 A1* | 6/2023 | Lin | A61B 34/30 700/245 |
| 2023/0210478 A1* | 7/2023 | Stopp | A61B 6/5211 378/1 |
| 2023/0225805 A1* | 7/2023 | Stopp | A61B 34/30 700/245 |
| 2023/0255699 A1* | 8/2023 | Ellman | A61B 34/30 700/245 |
| 2023/0255711 A1* | 8/2023 | Chaplin | A61B 34/30 606/1 |
| 2023/0263500 A1* | 8/2023 | Stopp | A61B 6/12 378/62 |
| 2023/0276016 A1* | 8/2023 | Frielinghaus | H04N 5/265 345/629 |
| 2023/0293248 A1* | 9/2023 | Ecke | G16H 40/63 600/437 |
| 2023/0293254 A1* | 9/2023 | Sarli | A61G 13/04 700/245 |
| 2023/0302652 A1* | 9/2023 | Kulkarni | B25J 9/1653 |
| 2023/0303342 A1* | 9/2023 | Kulkarni | B07C 5/36 |
| 2023/0320794 A1* | 10/2023 | Scholan | A61B 34/30 606/1 |
| 2023/0321694 A1* | 10/2023 | Hegde | B07C 5/28 209/577 |
| 2023/0321825 A1* | 10/2023 | Kulkarni | B25J 9/1697 700/260 |
| 2023/0346497 A1* | 11/2023 | Yang | A61B 90/00 |
| 2023/0355314 A1* | 11/2023 | Keret | A61B 90/39 |
| 2023/0355332 A1* | 11/2023 | Nagao | A61B 34/70 |
| 2023/0368887 A1* | 11/2023 | Roh | G05B 19/4155 |
| 2024/0001541 A1* | 1/2024 | Lin | A61B 34/37 |
| 2024/0139948 A1* | 5/2024 | Horiguchi | B25J 9/1671 |

FOREIGN PATENT DOCUMENTS

| | | | | |
|---|---|---|---|---|
| CN | 107106242 | | 6/2019 | |
| CN | 110430809 | | 11/2019 | |
| CN | 112088070 | | 12/2020 | |
| CN | 107198567 | | 2/2021 | |
| CN | 108451643 | | 2/2021 | |
| CN | 111434316 | | 6/2021 | |
| CN | 108778634 | | 7/2022 | |
| CN | 116648206 A * | 8/2023 | A61B 34/30 |
| EP | 1470791 A1 * | 10/2004 | A61B 34/20 |
| EP | 2017756 A1 * | 1/2009 | G06F 19/3406 |
| EP | 2332484 | | 6/2011 | |
| EP | 3694438 B1 * | 3/2021 | A61B 34/20 |
| JP | 2008284342 | | 11/2008 | |
| JP | 2008284342 A * | 11/2008 | A61B 34/20 |
| JP | 2020179466 | | 11/2020 | |
| JP | 6986017 | | 12/2021 | |
| JP | 2022533214 | | 7/2022 | |
| JP | 2022533214 A * | 7/2022 | |
| JP | 2023544317 A * | 10/2023 | |
| WO | 2016044574 | | 3/2016 | |
| WO | WO-2017028935 A1 * | 2/2017 | A61B 34/10 |
| WO | 20171344546 | | 8/2017 | |
| WO | WO-2017134546 A2 * | 8/2017 | A61B 34/30 |
| WO | 2021158738 | | 8/2021 | |

OTHER PUBLICATIONS

"Augmented Reality in Orthopedic Surgery Is Emerging from Proof of Concept Towards Clinical Studies: a Literature Review Explaining the Technology and Current State of the Art;" Casari et al.; Current Reviews in Musculoskeletal Medicine, 14(2), 192-203; Feb. 5, 2021. (Year: 2021).*

"On-the-fly Augmented Reality for Orthopaedic Surgery Using a Multi-Modal Fiducial;" Andress et al., J. Med. Imag. 5(2), 2018; Jan. 4, 2018 (Year: 2018).*

European Patent Office, International Search Report and Written Opinion corresponding to PCT/2017/071285 mailed date: Nov. 8, 2017. pp. 1-12.

Casari, et al., Augmented Reality in Orthopedic Surgery is Emerging from Proof of Concepts Towards Clinical Studies: a Literature Review Explaining the Technology and Current State of the Art, Feb. 5, 2021, 12 pages.

Cinquin, et al., Computer Assisted Medical Interventions, Sep. 18, 1995, 10 pages.

Zheng, et al., Computer-Assisted Orthopedic Surgery: Current State and Future Perspective, Dec. 23, 2015, 14 pages.

* cited by examiner

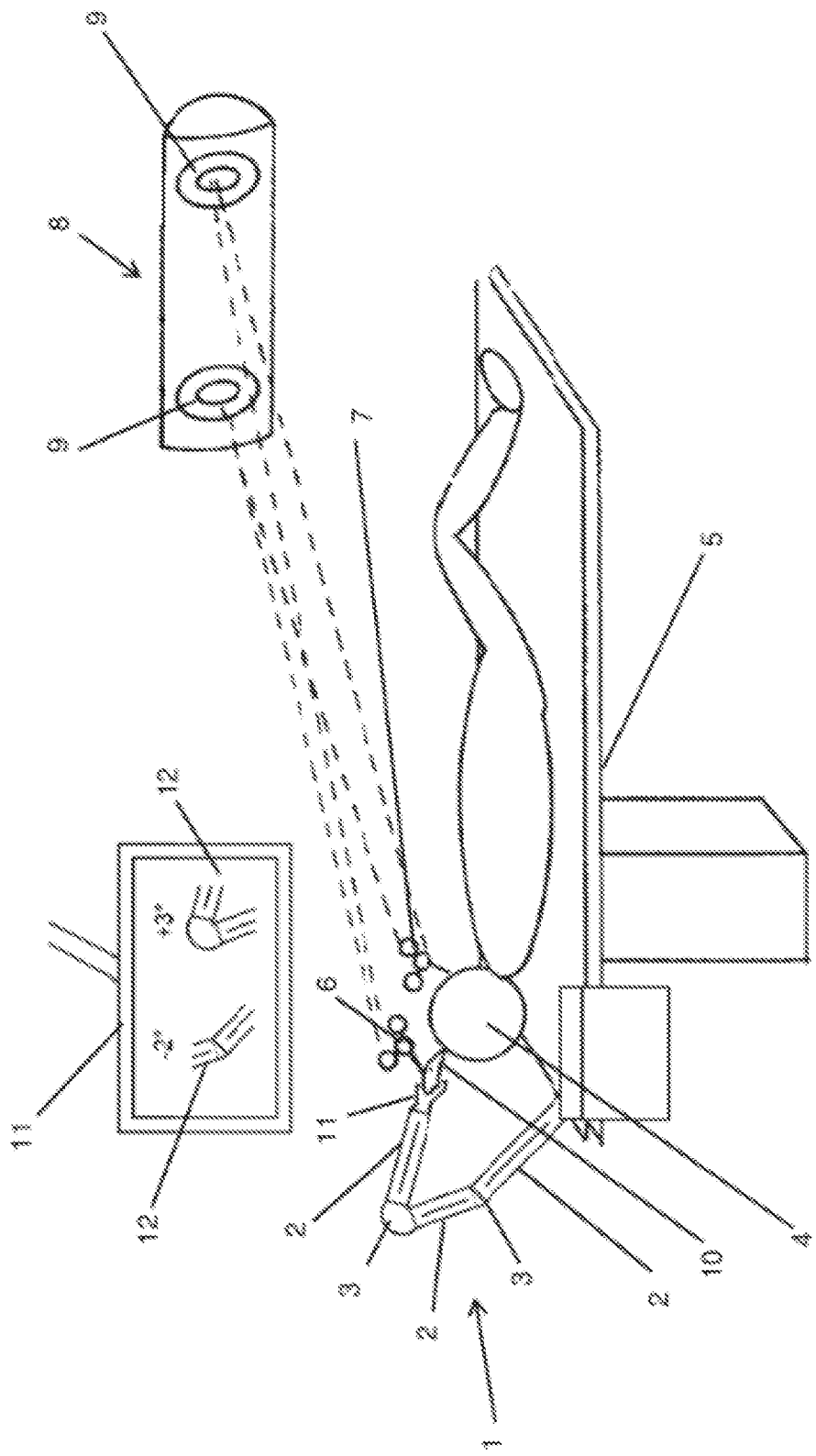

EFFICIENT POSITIONING OF A MECHATRONIC ARM

RELATED APPLICATION DATA

This application is a continuation of U.S. patent application Ser. No. 15/770,684 filed Apr. 24, 2018, which is a national phase application of International Application No. PCT/EP2017/071285 filed Aug. 24, 2017, published in the English language, which claims priority to Foreign Application No. PCT/EP2016/072957 filed Sep. 27, 2016, each of which is incorporated herein by reference in its entirety.

BACKGROUND

There are state-of-the-art products generally suitable for aligning a mechatronic articulable arm precisely to a target object such as an anatomical body part:
1) Stereotactic arcs are known in which joint positions for a highly rigid and reproducible hardware device are calculated and then adjusted manually based on a scale that is printed on the hardware.
2) Surgical robots are known that can automatically align to a trajectory.

The present invention is designed to provide a method and system for determining an efficient manner of positioning a mechatronic articulable arm relative to a target object.

Aspects of the present invention, examples and exemplary steps and their embodiments are disclosed in the following. Different exemplary features of the invention can be combined in accordance with the invention wherever technically expedient and feasible.

SUMMARY

In the following, a short description of the specific features of the present invention is given which shall not be understood to limit the invention only to the features or a combination of the features described in this section.

The present invention relates to a computer-implemented medical method for controlling the geometric status of a mechatronic articulable arm, a corresponding computer program, a non-transitory program storage medium storing such a program and a computer for executing the program, as well as a system for medical system for controlling the geometric status of a mechatronic articulable arm.

The disclosed method encompasses determining an instruction for adjusting the arm segments of a mechatronic articulable arm with optimum efficiency so that the distal end of the arm reaches a desired position relative to a target object such as an anatomical body part. To that end, the current position of the distal end relative to the anatomical body part is detected together with the current configuration of the arm segments, and a desired position of the distal end is input e.g. from a treatment plan for conducting an envisaged medical procedure using the mechatronic articulable arm. Together with information about the mechanical properties of the mechatronic articulable arm, the input data is input to an optimization algorithm for determining a change in the configuration of the arm segments so that the desired position of the distal end can be reached in an optimum manner (e.g. with as little operations on the arm segments as possible) from the current configuration of the arm segments.

DESCRIPTION OF GENERAL FEATURES

In this section, a description of the general features of the present invention is given for example by referring to possible embodiments of the invention.

In general, the invention reaches the aforementioned object by providing, in a first aspect, a computer-implemented medical method for controlling the geometric status of a mechatronic articulable arm.

The mechatronic articulable arm may be part of a robotic or semi-robotic system. A robotic system is understood to be a system which conducts operations exclusively on the basis of electronic commands received e.g. from or via a computer. A semi-robotic system is understood to be a system which conducts operations on the basis of both manual user intervention (e.g. for positioning at least a part of the system such as at least part of the mechatronic articulable arm) and electronic commands received e.g. from or via a computer. The mechatronic articulable arm comprises a plurality (i.e. at least two) arm elements which are connected to each other by joints such as turning joints or hinges and thus form connected elements of the mechatronic articulable arm. The connected elements can be moved relative to one another for example by rotating them (i.e. neighbouring elements) relative to one another (specifically, if they are connected via a turning joint, i.e. a swivel joint) around at least substantially around their longitudinal axes or by articulating them (i.e. neighbouring elements) relative to one another (specifically if they are connected via a hinge, for example articulating them relative to one another at an angle allowed by the hinge). Each connected element has a generally elongated shape and is for example rigid. The utility element comprises at least one of a medical tool or a fastening unit for fastening a medical tool. In one example, the utility element is located at the end (for example, the distal end) of the mechatronic articulable arm.

The method is for example a data processing method and comprises executing, on at least one processor of at least one computer (for example at least one computer being part of a navigation system usable for conducting a navigated medical procedure such as a surgical, more specifically neurosurgical, procedure), the following exemplary steps which are executed by the at least one processor.

In a (for example first) exemplary step, current device position data is acquired which describes (for example, defines or represents) a current relative position between a utility element of the mechatronic articulable arm and anatomical body part of a patient's body. The anatomical body part serves as an example of a target object and may be any body part but in a specific example comprises at least part of the patient's head or leg (such as the knee or the hip) or back (such as at least part of the spine). The current device position data is acquired in one example on the basis of electric signals generated by a navigation system such as an optical navigation system. Each a marker device may be positioned, for example attached, in a predetermined (for example, at least one of fixed or known) spatial relationship to both the utility element and the anatomical body part. If the utility element is the fastening unit, the relative position between the marker associated with the utility element and the medical tool is for example predetermined (for example, at least one of known or fixed), e.g. from constructional data for the utility element and the medical tool. The navigation system can track the position of each marker device (for example, in the reference system used to conduct the navigated medical procedure) by detecting reflections of light for example in the infrared wavelength range from markers in the marker devices, and generating electric signals corresponding to those positions, and converting those electric signals into the current relative position which is determined as digital data (for example, the current device position data).

In a further (for example second) exemplary step, current geometric status data is acquired which describes (for example, defines or represents) a current geometric status of the mechatronic articulable arm. The current geometric status defined by a set of at least one current spatial relationship (in one example, a plurality of, i.e. at least two current spatial relationships) between connected elements of the mechatronic articulable arm. Each spatial relationship defines for example uniquely the position of at least two (in one example, exactly two) neighbouring (i.e. adjacent) connected elements relative to each other. For example, the current geometric status is additionally defined by a unique assignment of the current spatial relationships to the pairs of neighbouring connected elements so that each spatial relationship is associated with a specific one of the pairs of neighbouring connected elements. For example, each spatial relationship is defined by at least one of a rotational angle defined around for example the longitudinal axes of the connected elements or a kink angle between for example the longitudinal axes of the connected elements. Alternatively or additionally, the spatial relationship is defined by the relative position between the associated neighbouring connected elements which is defined for example in a reference system such as a three-dimensional Cartesian or spherical coordinate system in which positions are defined for example for conducting a navigated medical procedure in which the mechatronic articulable arm is used. For example, the elements of the set of at least one current spatial relationship are defined by values of at least one of relative positions between the connected elements or angles between the connected elements. For example, at least one marker device called device marker device is attached to the mechatronic articulable arm in a predetermined (for example, at least one of known or fixed) spatial relationship to the utility element, and wherein the current device position data is acquired based on electric signals outputted by an optical navigation system configured to track the position of the device marker device.

In an alternative or additional example, the current device position data is acquired on the basis of predetermined (i.e. at least one of known or fixed) information about the position of at least a part of the mechatronic articulable arm (such as its base part) and the position of the anatomical body part for example in the reference system used to define positions for conducting the navigated medical procedure. Such predetermined information may be available for example from a predetermined plan for conducting the navigated medical procedure which has been determined before execution of the disclosed method starts. The position of the utility element may additionally be determined on the basis of the current geometric status data by taking into account the at least one current spatial relationship between the connected elements to determine, outgoing from the predetermined position of the at least part of the mechatronic articulable arm (such as the position of its base part, i.e. at least substantially most proximal part, i.e. the part at the end of the at least one mechatronic arm opposing the end at which the utility element is located), the position of the utility element.

In one example of this for example second exemplary step, the current geometric status data is acquired on the basis of electric signals generated by at least one encoder. For example, at least one (specifically, exactly one) encoder is associated with, for example positioned at least partly between, each pair of connected elements (specifically, each pair of neighbouring connected elements). The encoder is configured to determine the spatial relationship associated with the pair of connected elements and can be at least one of an optical, magnetic or capacitive encoder. Alternatively or additionally, the current geometric status data is acquired on the basis of electric signals generated by a navigation system such as an optical navigation system. Each a marker device may be positioned, for example attached, in a predetermined (for example, at least one of fixed or known) spatial relationship to each one of the connected elements forming a pair of neighbouring connected elements. The navigation system can track the position of each marker device (for example, in the reference system used to conduct the navigated medical procedure) by detecting reflections of light for example in the infrared wavelength range from markers in the marker devices, and generating electric signals corresponding to those positions, and converting those electric signals into the at least one current spatial relationship which is determined as digital data (for example, the current geometric status data).

In a further (for example third) exemplary step, device definition data is acquired which describes (for example, defines or represents) the movability of the mechatronic articulable arm. Generally, the movability of the mechatronic articulable arm defines the possible geometric statuses of the mechatronic articulable arm. The movability of the mechatronic articulable arm is defined for example by at least one of at least the degrees of freedom, for example of the connected elements of each pair of neighbouring connected elements relative to another, or at least the dimensions of at least the connected elements.

In a further (for example fourth) exemplary step, changed device position data is acquired which describes (for example, defines or represents) a changed relative position between the utility element and the anatomical body part. The changed relative position is a relative position between the utility element and the anatomical body part which is different from the current relative position between the utility element and the anatomical body part and is attained by the utility element and the anatomical body part later in time than the current relative position. Generally, the relative position between the utility element and the anatomical body part has changed compared to the current relative position when the utility element and the anatomical body part attain the changed relative position. The changed device position data is for example predetermined (i.e. known) before execution of the disclosed method starts and stored in a plan for conducting the navigated medical procedure. Alternatively, the changed device position data is generated during execution of the disclosed method, for example on the basis of information about the position of the anatomical body part for example in the reference system used to define positions for conducting the navigated medical procedure. The position of the anatomical body part may in one example be predetermined, and in another example may be determined by detecting for example a marker device attached to the anatomical body part (for example in a predetermined such as at least one of fixed or known spatial relationship) which is tracked by the navigation system to determine its position and therefore the position of the anatomical body part. Alternatively, the position of the anatomical body part may be determined by scanning reflections of structured light irradiated onto the anatomical body part and comparing them to a predetermined surface model of the anatomical body part which may have been generated from a computed x-ray tomography or magnetic resonance tomography of at least the surface of the anatomical body part.

In a further (for example fifth) exemplary step, changed geometric status data is determined which describes (for example, defines or represents) a changed geometric status of the mechatronic articulable arm. For example, the changed geometric status data is determined based on the current device position data and the current geometric status data and the changed device position data and the device definition data. The changed geometric status is defined by a set of at least one changed spatial relationship between the connected elements, wherein the set of at least one changed geometric relationship is different from the set of at least one current spatial relationship. The at least one changed spatial relationship can be defined in analogy to the definition of the at least one current spatial relationship described by the current geometric status data. For example, it can be described by at least one (desired) encoder position or at least one (desired) relative position between marker devices used for determining the relative position between the connected elements associated with the respective changed spatial relationship (i.e. which shall be attained in the changed geometric status). For example, the at least one element of the set of at least one changed spatial relationship is defined by values of at least one of at least one relative position between the connected elements or at least one angle between the connected elements.

In one example of this for example fifth exemplary step, the changed geometric status data is acquired by determining, taking into account the movability of the mechatronic articulable arm, the set of at least one current spatial relationship and the difference between the current relative position and the changed relative position between the utility element and the anatomical body part. Taking into account the movability of the mechatronic articulable arm for example supports avoiding determination of a changed geometric status which is not possible due to the mechanical and/or geometric properties of the mechatronic articulable arm. An optimization algorithm may be employed to determine how to change the geometric status of the mechatronic articulable arm from the current geometric status to the changed geometric status, considering for example at least one boundary condition such as a minimum of spatial relationships to be changed or a maximum amount by which each spatial relationship should be changed to achieve the change from the current geometric status to the changed geometric status. Further boundary conditions may encompass the avoidance of collisions with other entities or no-fly zones in which the utility element and/or the tool should not be positioned for example for safety reasons. Even further boundary conditions may encompass reduction of the influence of the envisaged medical procedure on the patient's tissue, for example if the mechatronic articulable arm is used in endoscopic surgery (for example on the spine). Even further, a boundary condition may be defined so that at least one joint connecting two connected elements is not articulated in the changed geometric state to an extent that no movability of the joint for correcting the geometric state of the joint is left. For example, the changed geometric state is determined such that the joint can still be operated in the changed geometric state, i.e. such that it keeps some freedom of movement.

The changed geometric status data is determined for example by applying a numerical optimization method, for example the Jacobian Pseudo-Inverse method, to the current geometric status data and considering the current device position data and the changed device position data as boundary conditions. The input data to such an optimization method may include the forward kinematics of the mechatronic articulable arm (i.e. the algorithm for calculating the changed geometric status based on the output signals of the at least one encoder and/or based on positions of marker devices attached the connected elements), the current geometric status data, the changed device position data and (at least the value of) a merit function for determining the quality (e.g. the efficiency) of achievability of the changed geometric status (depending e.g. on the number of spatial relationships to be changed). The optimization method will output the encoder positions and/or the positions of the marker devices associated with the changed geometric status.

In a further (for example sixth) exemplary step, instruction data is determined which describes (for example, defines or represents) an instruction for changing the geometric status of the mechatronic articulable arm from the current geometric status to the changed geometric status. For example, the instruction data is determined based on the current geometric status data and the changed geometric status data. In one example, wherein the instruction comprises information how to adjust (for example, manually adjust) the at least one spatial relationship between the connected elements, for example in which direction (and for example by which amount) to move the connected elements relative to each other [for example, turning or kinking a joint]. The direction (and for example amount) of moving the connected elements relative to each other is for example determined so that the associated pair of neighbouring connected elements attains, at least within a predetermined interval, the changed spatial relationship. For example the direction (and for example amount) of moving the connected elements relative to each other is determined so that the associated at least one encoder attains, for example at least within a predetermined interval, the at least one encoder position which shall be attained in the changed geometric status, or so that at least one relative position between marker devices used for determining the relative position between the connected elements becomes, for example at least within a predetermined interval, becomes the desired relative position. The instruction is in one example outputted to a user, for example by using a visual output device (such as at least one of a monitor and/or computer display, or at least one display element—such as a light element—on the robotic arm) or an acoustic output device (such as a loudspeaker) or a tactile output device (such as a vibration element located for example on the robotic arm).

In one example of this for example sixth exemplary step, a check can be conducted as to whether the desired geometric status of the mechatronic articulable arm has been reached. To this end, the disclosed method may comprise the following steps:

acquiring, at the at least one processor, encoder position data describing (for example, defining or representing) the position of the at least one encoder;

determining, based on the encoder position data and the changed geometric status data, spatial relationship check data describing (for example, defining or representing) whether at least one spatial relationship between the connected elements is, for example at least within a predetermined interval, equal to the at least one changed spatial relationship.

The encoder position data can be generated from electronic signals issued by the at least one encoder and converted into digital data. The spatial relationship check data can be determined by comparing the position of the at least one encoder to an encoder position associated (at least within a predetermined interval) with the at least one changed spatial relationship.

Such a check may be used to determine whether the joints connecting the connected elements should be automatically locked. To this end, the disclosed method may comprise the following step:

determining, by the at least one processor and based on the encoder check data (for example, if the spatial relationship check data describes (for example, defines or represents) that the at least one spatial relationship between the connected elements is, at least within a predetermined interval, equal to the at least one changed spatial relationship), lock signal data describing (for example, defining or representing) a control signal to be issued to the mechatronic articulable arm for locking the spatial relationship between the connected elements in their current position, for example by activating a locking mechanism configured to lock a joint connecting the connected elements.

In a further example of the for example sixth exemplary step, the number of connected elements is at least three and the instruction data is determined by determining an order in which the at least two spatial relationships between the connected elements shall be adjusted. In this example, the method may be executed after each adjustment of one of the at least two spatial relationships between the connected elements.

In more specific examples, the order in which the at least two spatial relationships between the connected elements shall be adjusted is arranged such that at least one of the following conditions i) to iv) is fulfilled:

i) if the joints have a predetermined resolution of joint positions (defined for example by the mechanical properties of the joints allowing for example only for discrete joint positions), the joints are placed in the order in dependence on their mechanical resolution, for example such that a joint will be adjusted earlier the coarser its mechanical resolution is;

ii) the joints will be adjusted in dependence on their distance from a base part of the mechatronic articulable arm;

iii) the joints are placed in the order in dependence on the type of joint they belong to, for example depending on whether a joint is a swivel joint or a hinge;

iv) the joints are placed in the order in dependence on their movability, for example such that a joint will be adjusted earlier the less degrees of freedoms it has.

If the number of connected elements is at least three and the set of at least one changed spatial relationship between the connected elements comprises only a minimum number of spatial relationships changed to achieve the changed geometric status, the instruction data may describe (for example, defines or represents) an instruction for changing only the respective at least one current spatial relationship to the respective at least one changed spatial relationship.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a fifth aspect, the invention is directed to a (physical, for example electrical, for example technically generated) signal wave, for example a digital signal wave, carrying information which represents the program according to the second aspect.

In a sixth aspect, the invention is directed to a medical system for controlling the geometric status of a mechatronic articulable arm, the medical system comprising:

a) the at least one computer according to the fourth aspect;
b) at least one output device;
c) the mechatronic articulable arm; and
d) at least one electronic data storage device storing at least one of the changed device position data or the device definition data, wherein the at least one computer is operably coupled to the at least one electronic data storage device for acquiring, from the at least one data storage device, at least one of the changed device position data or the device definition data, wherein the at least one computer is operably coupled to the mechatronic articulable arm for acquiring, from the mechatronic articulable arm, electric signals corresponding to the current device position data or the current geometric status data, and wherein the at least one computer is operably coupled to the at least one output device for transmitting, to the output device the instruction data and controlling the output device to output the instruction.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a computer-based navigation system and can be a stereotactic camera which is sensitive to electromagnetic waves in a predetermined wavelength range such as the infrared wavelength range or any other wavelength range with which the marker are irradiated and which is reflected by the marker. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A navigation system can be a navigation system for computer-assisted surgery. This navigation system preferably comprises the aforementioned computer according to the fourth aspect for processing the data provided in accordance with the computer implemented method as described in any one of the embodiments described herein. The navigation system preferably comprises a detection device for detecting the position of a marker device such as an optical emitter (operating e.g. in the infrared wavelength range) for emitting light and an optical detector (e.g. a stereotactic camera) for detecting reflections generated by reflection of the light emitted by the optical emitter from the marker device, and transforming the signals corresponding to the reflections into digital data comprising information representing the position of the marker device. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

BRIEF DESCRIPTION OF THE DRAWINGS

In the following, the invention is described with reference to the appended figures which represent a specific embodiment of the invention. The scope of the invention is however not limited to the specific features disclosed in the context of the figures, wherein

FIG. 5 is an overview of the system in accordance with the sixth aspect.

DETAILED DESCRIPTION

Figure 1:
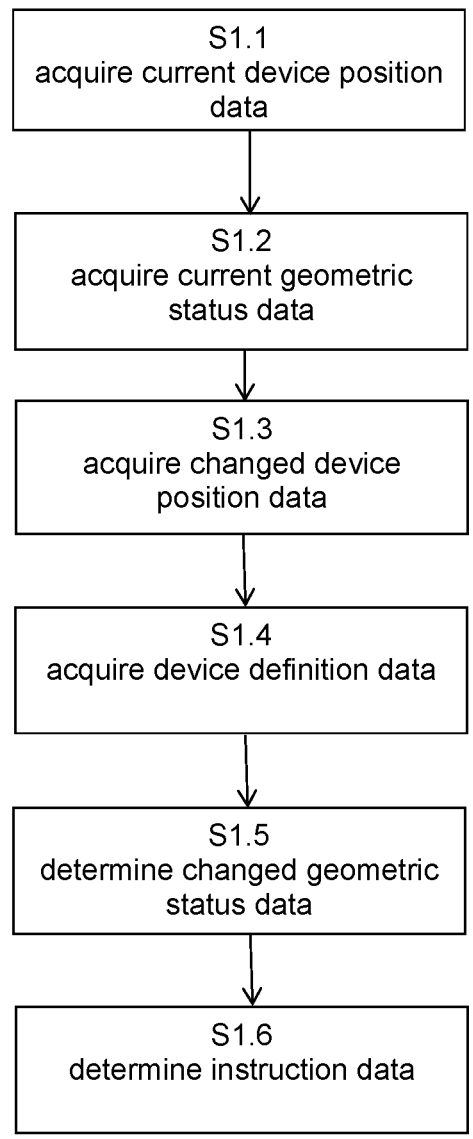
FIG. 1 is a flow diagram illustrating the basic steps of the disclosed method according to the first aspect.

FIG. 1 is a flow diagram illustrating the basic steps of the disclosed method in accordance with the first aspect, which in the illustrative example of FIG. 1 starts with a step S1.1 of acquiring the current device position data. In subsequent step S1.2, the current geometric status data is acquired, followed by step S1.3 which encompasses acquiring the changed device position data. Then, step S1.4 acquires the device definition data. Step S1.5 uses steps S1.1, S1.2, S1.3 and S1.4 as input steps and is directed to determining the changed geometric status data. Finally, the instruction data is determined in step S1.6.

Figure 2:
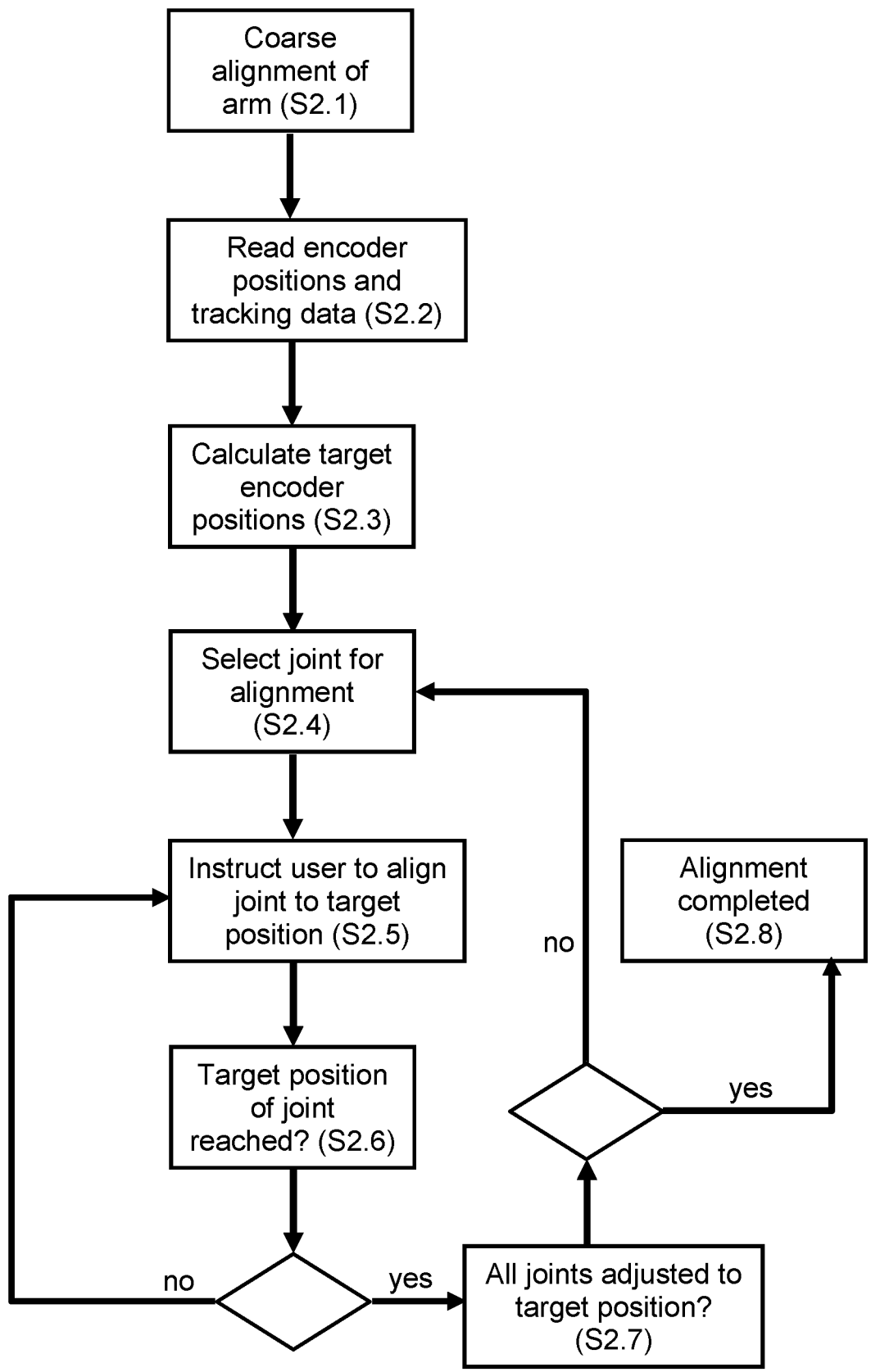
FIG. 2 is a flow diagram illustrating a general flow of method for aligning the mechatronic arm.

FIG. 2 shows how the method in accordance with the first aspect can be integrated into a practical approach: in step S2.1, the mechatronic articulable arm is coarsely aligned (positioned) relative to the anatomical body part (for example, by manual user interaction). In step S2.2, the encoder positions are read and converted into the current geometric status data and the tracking data is read and converted into the current device position data. On the basis of the data read in step S2.2 and the device definition data, the target encoder positions are calculated in step S2.3 and stored as the changed geometric status data. Then, a joint between two connected elements of the mechatronic articulable arm is selected for alignment (i.e. adjustment) in step S2.4. The instruction data is determined in step S2.5 and the instruction is output to a user for example on a display device such as a monitor 11. By determining the spatial relationship check data, it is determined in step S2.6 whether the target position of the joint adjusted according to the instruction output in step S2.5 has reached its target position. If this is not the case, the method returns to step S2.5. If step S2.6 determines that the target position has been reached, the method continues with step S2.7 which involves determining whether all joints of the mechatronic articulable arm have been adjusted to their respective target position as defined by the changed geometric status data. If all joints are determined to have been adjusted to their target position, the method end in step S2.8 because the alignment of the mechatronic articulable arm has been completed. If step S2.7 determines that not all joints have reached their target position, the method returns to step S2.4.

Figure 3:
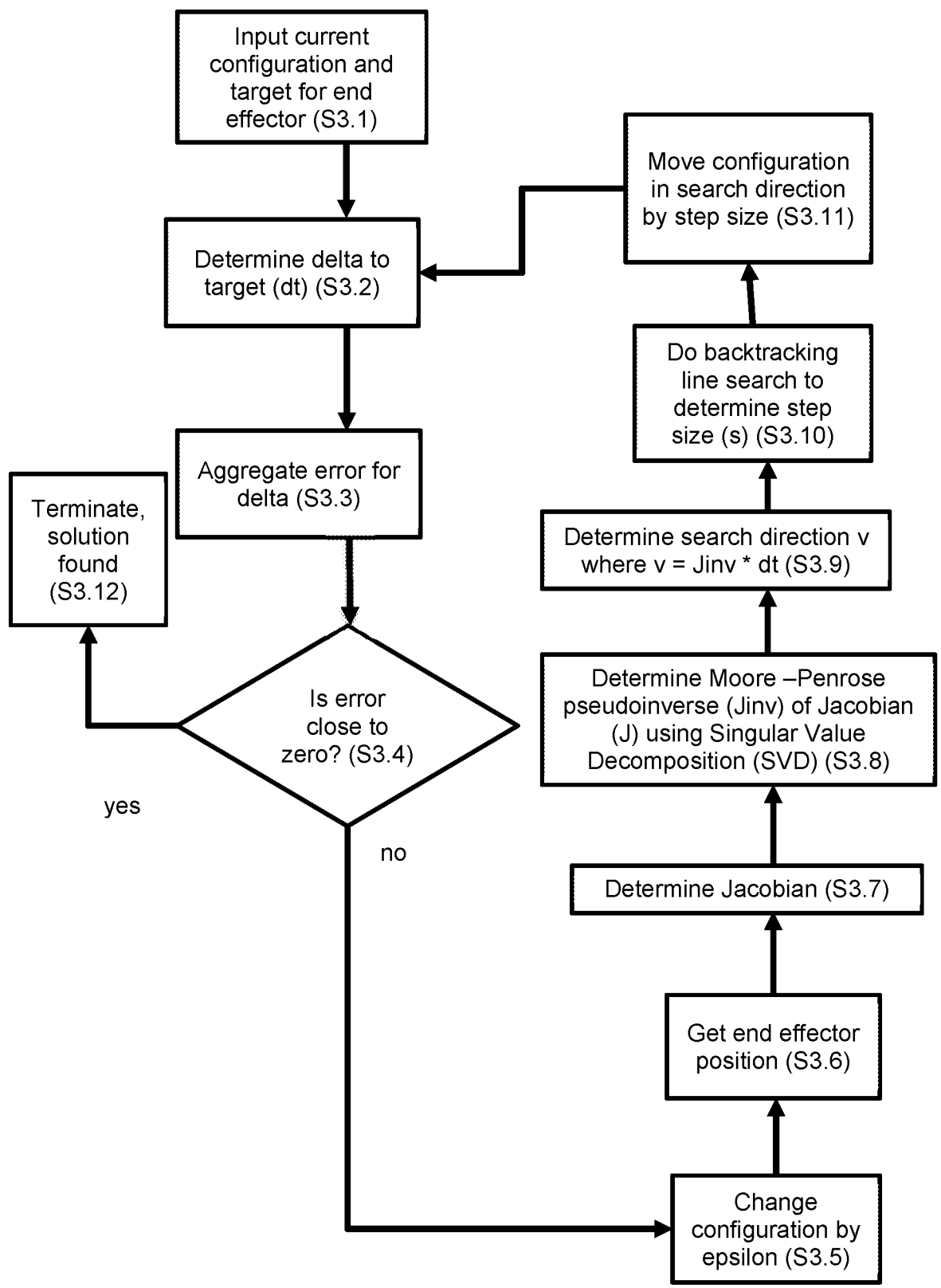
FIG. 3 is a first embodiment of the optimization method for determining the changed geometric status data.
Figure 4:
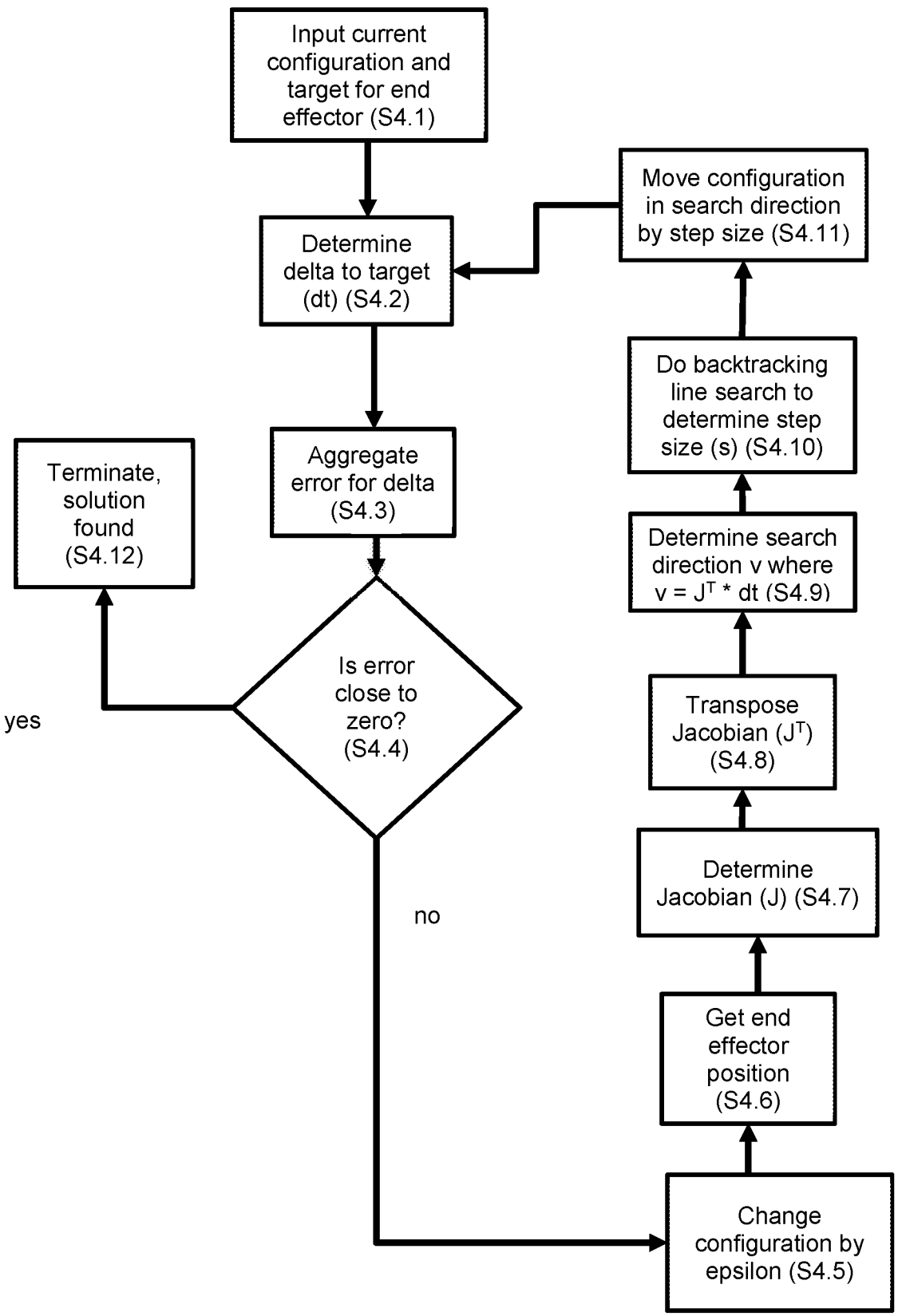
FIG. 4 is a second embodiment of the optimization method for determining the changed geometric status data.

FIGS. 3 and 4 illustrate two different approaches for the optimization algorithm used to determine the changed geometric status data, wherein steps S3.1, S3.2, S3.3, S3.4, S3.5, S3.6, S3.10, S3.11 and S3.12 of FIG. 3 correspond respectively to steps S4.1, S4.2, S4.3, S4.4, S4.5, S4.6, S4.7, S4.10, S4.11 and S4.12 of FIG. 4. The description of those steps in the context of FIG. 3 therefore also applies to the respective steps of FIG. 4. Duplicate description of corresponding steps is omitted herein.

In step S3.1. of FIG. 3, the current configuration of the mechatronic articulable arm is input by acquiring the current geometric status data, and the target position of the end effector representing the utility element (i.e. the changed device position). Then the difference between the current geometric status and the changed geometric status is determined as dt in step S3.2, and an error associated with this difference is determined in step S3.3 by comparing the changed device position data to the desired relative position between the utility element and the anatomical body part. For example, a difference is computed between the coordinates of the changed relative position described by the changed device position data and the coordinates of the desired position and/or the trajectory (defined e.g. in Euler angles) along which the utility element is moved. The optimisation may be directed to the changed relative position independently of the associated trajectory for achieving the changed relative position, to the changed relative position along with a direction of the trajectory and free rotation along the direction in five degrees of freedom or a movement fully defined in six degrees of freedom. The method determines in step S3.4 whether the error is close to zero, and if this is the case, terminates in step S3.12 because it is then determined that the solution for the changed geometric status has already been found. A corresponding instruction can then be issued to the user to tell him how to manually adjust the mechatronic articulable arm to bring it into the changed geometric status. If step S3.4 determines that the error is not close to zero, the method continues to step S3.5 which encompasses a change of the configuration (the geometric status) by an increment epsilon and determining the position of the end effector (utility element) for the incremented configuration in step S3.6. Then, the Jacobian of the encoder values is determined in step S3.7 (the Jacobian matrix includes the first derivative of the encoder values). Subsequent step S3.8 continues with determining the Moore-Penrose pseudoinverse (Jinv) of the Jacobian J using singular value decomposition (SVD). Once Jinv has been determined, a search direction v for searching for further changes to the geometric status can be determined by solving v=Jinv*dt in step S3.9, wherein * denotes the multiplication operator. A backtracking line search is then conducted in step S3.10 to determine a steps size s for changing the geometric status in step S3.10. Using that steps size s, the method calculates a changed geometric status in step S3.11, and then returns to step S3.2 using the changed geometric status as an input.

Steps S3.8 and S3.9 of FIG. 3 have been replaced by steps S4.8 and S4.9 in FIG. 4. Step S3.8 encompasses determining the transpose $J^T$ of the Jacobian J of the encoder values determined in step S4.7. Step S4.9 then determines the search direction v for which v=$J^T$*dt, wherein * is the operator of multiplication. Otherwise, the method of FIG. 4 corresponds to the method FIG. 3.

The order in which the joints shall be adjusted can be determined by applying a method on the basis of the following pseudocode named "Joint positioning order":

Joint Positioning Order

```
get current joint configuration // input of current geometric status
calculate target configuration // determine changed geometric status
for each joint in joints
{
    if joint position not at target position remember joint
}
sort all remembered joints from lowest precision joint to highest precision joint
for each joint in sorted joints
{
    open joint
    while joint not marked as reached
    {
        give user instruction
        if joint position == target position +- epsilon
        {
            mark as target position reached
        }
    }
}
```

The changed geometric status can be determined in an optimized manner by applying a method on the basis of the following pseudocode named "Target configuration refined":

Target Configuration Refined

```
for N = 1 to total number of joints
{
    for each permutation P of N joints in total number of permutations of N joints
    {
        calculate target configuration using only joints in P
        determine delta to target (dt) with target configuration
        if dt below epsilon
        {
            remember dt
        }
    }
    if any P where dt below epsilon
    {
        get P with smallest dt and terminate loop
    }
}
for lowest position joint to highest position joint in P
{
    open joint
    while joint not marked as target reached
    {
        give user instruction
        if joint position == target position +- epsilon
        {
            mark joint as target position reached
            calculate target configuration with joints in P not yet at marked as target reached
            update target configuration
        }
    }
}
```

FIG. 5 shows a setup of a system according to the sixth aspect. A patient having a head 4 as an anatomical body part 4 is placed on a support device embodied by a couch 5. A mechatronic articulable arm 1 is attached to the couch 5. The mechatronic articulable arm 1 comprises three segments 2 representing the connected elements. Each a pair of the segments is connected by a joint 3. Disposed at the distal end of the mechatronic articulable arm 1 is a utility element comprising a fastening unit 11 for fastening a medical instrument (a medical tool) 10 to which a marker device represented by a reference star 6 is attached. Another marker device 7 is attached to the patient's head 4, and both marker devices 6, 7 are tracked by a navigation system having an optical tracking unit 8 including a stereoscopic camera 9. The camera 9 outputs detection signals to a computer of the navigation system (not shown) to generate the current device position data. The instruction data is output on a display device embodied by a monitor 11 as visual instructions 12 so that a user can tell by which angle to manually adjust the individual joints 3.

The invention comprises the following features:

- A mechatronic holding arm with internal position sensors (e.g. optical or magnetic encoders) is used that means that the arm can communicate the absolute position (based on absolute encoders or using relative encoders with a nulling procedure) of one or multiple of its joints to the navigation system
- The instrument held by the arm is tracked and the relative position of the instrument to the arm is known— alternatively, the arm could be tracked as well
- The body part of interest is tracked and one or multiple target positions (e.g. trajectories) are planned (pre- or intra-operatively)

The precise alignment is now performed according the following procedure:

1. The user performs a rough alignment to a selected target position (with the help of the navigation system) such that the instrument is in the tracking range by the navigation system.
2. Based on the instrument position in relation to the body part, the relative position of the instrument to the arm and the forward kinematics (=adding up the dimensions of the different arm segments with the respective current e.g. rotational position known by the encoders) of the arm system, the presumed position of the arm base relative to the body part is calculated.
3. Based on the selected target position, the presumed position of the arm base, the relative position of the instrument to the arm and the inverse kinematics of the arm system (calculated using e.g. a numerical optimization method such as the "Jacobian Pseudo-Inverse" technique) a set of target encoder positions is calculated.
4. Instructions are provided to the user to adjust the joint positions manually until they match the calculated target encoder positions.

Several options are possible in this procedure:

- The instructions provided may be joint by joint (e.g. also only unlocking one joint at a time) or comprise multiple joints at a time.
- The calculation may use only a subset of joints provided by the arm if the alignment only requires a certain number of degrees of freedom.
- The calculation may try out different subsets of joints if not all joints are required thereby figuring out the smallest or most convenient subset required to perform the alignment up to a certain accuracy threshold (defined by e.g. distance of target and entry point to the presumed target position).
- If the alignment is performed joint by joint, the calculation can be rerun after the alignment of each joint such that small errors during the alignment of an earlier joint might be mitigated by the alignment of the subsequent joints.
- The calculation may avoid certain joint configurations if these may cause the arm to hit the patient or other tracked instruments The joints can be locked automatically if the target encoder position is reached within a certain threshold.
- The instructions may be provided on the navigation screen or via feedback methods of the mechatronic arm such as LED's.
- The instructions may comprise the representation of the target state of the mechatronic arm as a 3-D rendering on the navigation screen.
- The instructions may be provided in an acoustic fashion e.g. similar to a park-distance control.
- The instructions may include an indication in what direction a joint should to be turned to reach its target encoder position.

The purpose of the invention is to provide a method that allows to align a passive mechatronic holding arm precisely and efficiently to one or multiple targets. Passive mechatronic holding arms are an interesting hybrid of a traditional holding arm and a classical robotic arm in the way that they offer all features of a robotic arm except for the actuation which is thus replaced by human labour. The removal of the motors allows to come up with a much simpler, lighter and safer device. By combining a passive mechatronic holding arm with the guidance provided by a navigation system one is able to come up with a system that can still perform well in terms of accuracy and convenience of the alignment.

The technical effect of the invention is that the instrument can be aligned to the target position precisely with relative convenience for the user without having to use a more complex, heavier, larger, riskier and less cost-efficient robotic system.

The invention claimed is:

1. A computer-implemented method executed on at least one processor of at least one computer for controlling a geometric status of a mechatronic articulable arm, the method comprising:

acquiring, at the at least one processor, current device position data describing a current relative position between a utility element of the mechatronic articulable arm and an anatomical body part of a patient's body;

acquiring, at the at least one processor, current geometric status data describing a current geometric status of the mechatronic articulable arm defined by a set of at least one current spatial relationship between connected elements of the mechatronic articulable arm, wherein each spatial relationship defines a position of at least two neighbouring connected elements relative to each other, the at least two neighbouring connected elements connected by at least one joint;

acquiring, at the at least one processor, changed device position data describing a changed relative position between the utility element and the anatomical body part that is a relative position that has changed compared to the current relative position;

acquiring, at the at least one processor, device definition data describing movability of the mechatronic articulable arm;

determining, by the at least one processor and based on the current device position data and the current geometric status data and the changed device position data and the device definition data, changed geometric status data describing a changed geometric status of the mechatronic articulable arm defined by a set of at least one changed spatial relationship between the connected elements, wherein the changed geometric status is determined such that joints connecting neighbouring connected elements retain freedom of movement in the changed geometric status such that neighbouring connected elements remain moveable relative to each other, wherein the set of at least one changed geometric relationship is different from the set of at least one current spatial relationship, the set of at least one changed spatial relationship between the connected elements comprising a minimized number of spatial relationships changed to achieve the changed geometric status, the minimized number representing a number of joints being repositioned to achieve the changed geometric status;

determining, by the at least one processor and based on the current geometric status data and the changed geometric status data, instruction data describing an instruction to be presented to an associated user for manually changing the geometric status of the mechatronic articulable arm from the current geometric status to the changed geometric status, wherein changing the geometric status of the mechatronic articulable arm from the current geometric status to the changed geometric status defines a change in configuration of the connected elements, the instruction describing changes from the respective at least one current spatial relationship to the respective at least one changed spatial relationship; and outputting, by the at least one processor, the instruction to the associated user via an associated output device for selective use by the associated user in controlling the geometric status of the mechatronic articulable arm.

2. The method according to claim 1, wherein the acquiring the current geometric status data comprises acquiring the current geometric status data based on electric signals generated by at least one encoder associated with the connected elements, and wherein the changed geometric status data describes at least one encoder position which shall be attained in the changed geometric status.

3. The method according to claim 1, wherein the determining the instruction comprises determining information describing an adjustment to be made to at least one spatial relationship between the connected elements.

4. The method according to claim 3, wherein the determining the information describing the adjustment to be made to the at least one spatial relationship between the connected elements comprises determining a direction to move the connected elements relative to each other so that an associated at least one encoder attains an at least one encoder position that shall be attained in the changed geometric status.

5. The method according to claim 3, further comprising:
acquiring, by the at least one processor, encoder position data describing a position of at least one encoder; and
determining, based on the encoder position data and the changed geometric status data, spatial relationship check data describing whether at least one spatial relationship between the connected elements is equal to the at least one changed spatial relationship.

6. The method according to claim 5, further comprising:
determining, by the at least one processor and based on the spatial relationship check data, lock signal data describing a control signal to be issued to the mechatronic articulable arm that locks the spatial relationship between the connected elements in their current position.

7. The method according to claim 1, wherein the determining the instruction data comprises determining an order in which at least two spatial relationships between the connected elements shall be adjusted, wherein a number of connected elements of the mechatronic articulable arm comprises at least three connected elements.

8. The method according to the claim 7, wherein the determining the order comprises determining an order that is arranged such that at least one of the following conditions i) to iv) is fulfilled:
the joints connecting the connected elements of the mechatronic articulable arm are placed in order in dependence on their mechanical resolution;
ii) the joints connecting the connected elements of the mechatronic articulable arm are adjusted in dependence on their distance from a base part of the mechatronic articulable arm;
iii) the joints connecting the connected elements of the mechatronic articulable arm are placed in order in dependence on which type of joint they belong;
iv) the joints connecting the connected elements of the mechatronic articulable arm are placed in order in dependence on their movability.

9. The method according to claim 7, further comprising repeatedly executing the method after each adjustment of one of the at least two spatial relationships between the connected elements.

10. The method according to claim 1, wherein the determining the changed geometric status data comprises applying a numerical optimization to the current geometric status data using the current device position data and the changed device position data as boundary conditions.

11. The method according to claim 10, wherein the applying the numerical optimization comprises applying a Jacobian Pseudo-Inverse numerical optimization to the current geometric status data.

12. The method according to claim 1, wherein the elements of the set of at least one current spatial relationship are defined by values of at least one of relative positions between the connected elements or angles between the connected elements, and wherein at least one element of the set of at least one changed spatial relationship is defined by values of at least one of at least one relative position between the connected elements or at least one angle between the connected elements.

13. The method according to claim 1, wherein the acquiring the device definition data describing the movability of the mechatronic articulable arm comprises acquiring device definition data that describes movability of the mechatronic articulable arm defined by at least one degree of freedom or at least one dimension of at least one of the connected elements.

14. The method according to claim 1, wherein the acquiring the current geometric status data comprises acquiring current geometric status data that describes a current geometric status of a mechatronic articulable arm that is part of a robotic or semi-robotic system.

15. The method according to claim 1, further comprising attaching at least one marker device to the mechatronic articulable arm in a predetermined spatial relationship to the utility element, and wherein the acquiring the current device position data comprises acquiring the current device position data based on electric signals outputted by an associated optical navigation system configured to track the position of the marker device attached to the mechatronic articulable arm.

16. The method according to claim 1, further comprising attaching at least one marker device to the patient's body in a predetermined spatial relationship to the anatomical body part, and wherein the acquiring the current device position data comprises acquiring the current device position data based on electric signals outputted by an associated optical navigation system configured to track the position of the marker device attached to the patient's body.

17. The method according to claim 1, wherein the utility element of the mechatronic articulable arm comprises at least one of a medical tool or a fastening unit for fastening a medical tool, wherein the acquiring the current device position data comprises acquiring current device position data describing a current relative position between at least one of the medical tool of the mechatronic articulable arm or the fastening unit of the mechatronic articulable arm for fastening the medical tool and the anatomical body part of the patient's body.

18. The method according to claim 1, wherein the acquiring the current geometric status comprises acquiring a current geometric status that is defined by a unique assignment of the at least one current spatial relationship to pairs of adjacent connected elements so that each spatial relationship is associated with a specific one of the pairs of adjacent connected elements.

19. A medical system for controlling a geometric status of a mechatronic articulable arm, the medical system comprising:
   at least one output device;
   the mechatronic articulable arm comprising connected elements; and
   a computer configured to:
      acquire current device position data describing a current relative position between a utility element of the mechatronic articulable arm and an anatomical body part of a patient's body;
      acquire current geometric status data describing a current geometric status of the mechatronic articulable arm defined by a set of at least one current spatial relationship between the connected elements of the mechatronic articulable arm, wherein each spatial relationship defines a position of at least two neighbouring connected elements relative to each other, the at least two neighbouring connected elements connected by at least one joint;
      acquire changed device position data describing a changed relative position between the utility element and the anatomical body part that is a relative position that has changed compared to the current relative position;
      acquire device definition data describing movability of the mechatronic articulable arm;
      determine, based on the current device position data and the current geometric status data and the changed device position data and the device definition data, changed geometric status data describing a changed geometric status of the mechatronic articulable arm defined by a set of at least one changed spatial relationship between the connected elements, wherein the changed geometric status is determined such that joints connecting neighbouring connected elements retain freedom of movement in the changed geometric status such that neighbouring connected elements remain moveable relative to each other, wherein the set of at least one changed geometric relationship is different from the set of at least one current spatial relationship, the set of at least one changed spatial relationship between the connected elements comprising a minimized number of spatial relationships changed to achieve the changed geometric status, the minimized number representing a number of joints being repositioned to achieve the changed geometric status;
      determine, based on the current geometric status data and the changed geometric status data, instruction data describing an instruction for manually changing the geometric status of the mechatronic articulable arm from the current geometric status to the changed geometric status, wherein changing the geometric status of the mechatronic articulable arm from the current geometric status to the changed geometric status defines a change in configuration of the connected elements, the instruction describing changes from the respective at least one current spatial relationship to the respective at least one changed spatial relationship; and
      output the instruction to the at least one output device for controlling the geometric status of the mechatronic articulable arm.

20. A non-transitory computer readable storage medium storing a program for controlling a geometric status of a mechatronic articulable arm, that when executed on at least one processor of a computer or loaded onto the at least one processor of the computer, causes the computer to:
   acquire current device position data describing a current relative position between a utility element of the mechatronic articulable arm and an anatomical body part of a patient's body;
   acquire current geometric status data describing a current geometric status of the mechatronic articulable arm defined by a set of at least one current spatial relationship between connected elements of the mechatronic articulable arm, wherein each spatial relationship defines a position of at least two neighbouring connected elements relative to each other, the at least two neighbouring connected elements connected by at least one joint;
   acquire changed device position data describing a changed relative position between the utility element and the anatomical body part that is a relative position that has changed compared to the current relative position;
   acquire device definition data describing movability of the mechatronic articulable arm;
   determine, based on the current device position data and the current geometric status data and the changed device position data and the device definition data, changed geometric status data describing a changed geometric status of the mechatronic articulable arm defined by a set of at least one changed spatial relationship between the connected elements, wherein the changed geometric status is determined such that joints connecting neighbouring connected elements retain freedom of movement in the changed geometric status such that neighbouring connected elements remain moveable relative to each other, wherein the set of at least one changed geometric relationship is different from the set of at least one current spatial relationship, the set of at least one changed spatial relationship between the connected elements comprising a minimized number of spatial relationships changed to achieve the changed geometric status, the minimized number representing a number of joints being repositioned to achieve the changed geometric status;
   determine, based on the current geometric status data and the changed geometric status data, instruction data describing an instruction for manually changing the geometric status of the mechatronic articulable arm from the current geometric status to the changed geometric status, wherein changing the geometric status of the mechatronic articulable arm from the current geometric status to the changed geometric status defines a change in configuration of the connected elements, the instruction describing changes from the respective at least one current spatial relationship to the respective at least one changed spatial relationship; and output the instruction to at least one associated output device to control the geometric status of the mechatronic articulable arm.

\* \* \* \* \*